United States Patent [19]

Fellmann et al.

[11] Patent Number: 4,861,921
[45] Date of Patent: Aug. 29, 1989

[54] PROCESS FOR MANUFACTURE OF RESORCINOL

[76] Inventors: Jere D. Fellmann, 1474 Lexington Way, Livermore, Calif. 94550; Robert J. Saxton, 1460 Lewiston Dr., Sunnyvale; Paul Tung, 908 Exmoor Way, both of Sunnyvale, Calif. 94087

[21] Appl. No.: 21,219

[22] Filed: Mar. 3, 1987

Related U.S. Application Data

[63] Continuation-in-part of Ser. No. 840,838, Mar. 18, 1986, abandoned.

[51] Int. Cl.$^4$ ............................................. C07C 37/06
[52] U.S. Cl. ..................................... 568/772; 568/771
[58] Field of Search ................................ 568/771, 772

[56] References Cited

U.S. PATENT DOCUMENTS

| | | | |
|---|---|---|---|
| 3,476,808 | 11/1969 | Etherington et al. | 568/772 |
| 3,673,255 | 6/1972 | Etherington et al. | 568/772 |
| 3,965,187 | 6/1976 | Little et al. | 568/772 |
| 4,018,833 | 4/1977 | Muller et al. | 568/772 |
| 4,024,196 | 5/1977 | Krekelev et al. | 568/772 |
| 4,072,660 | 2/1978 | Müller et al. | 568/772 |
| 4,154,762 | 5/1979 | Huang et al. | 568/772 |
| 4,154,965 | 5/1979 | Meijer et al. | 568/772 |
| 4,160,113 | 7/1979 | Müller et al. | 568/772 |
| 4,192,958 | 3/1980 | Hashimoto et al. | 568/763 |
| 4,200,553 | 4/1980 | Van Peppen et al. | 568/772 |
| 4,229,597 | 10/1980 | Taguchi et al. | 568/768 |
| 4,239,921 | 12/1980 | Hashimoto et al. | 568/768 |
| 4,250,336 | 2/1981 | Müller et al. | 568/772 |
| 4,273,623 | 6/1981 | Hashimoto et al. | 568/772 |
| 4,283,567 | 8/1981 | Nambu et al. | 568/754 |
| 4,283,570 | 8/1981 | Nakagawa et al. | 568/772 |
| 4,347,393 | 8/1982 | Miki | 568/772 |
| 4,377,709 | 3/1983 | Muller | 568/459 |
| 4,417,076 | 11/1983 | Rozovsky et al. | 568/772 |
| 4,431,848 | 2/1984 | Greco | 568/772 |

FOREIGN PATENT DOCUMENTS

| | | |
|---|---|---|
| 951742 | 7/1974 | Canada . |
| 107253 | 7/1974 | Fed. Rep. of Germany . |
| 49-127909A | 12/1974 | Japan . |
| 1188387 | 4/1970 | United Kingdom . |

OTHER PUBLICATIONS

J. Molecular Catalysis, 21 (1983) 393–404, "Selective Hydrogenation of Benzene to Cyclohexene with Zircomium Hydride Catalysts".
J. Org. Chem., 1980, 45, 4278–4280, "Base-Catalyzed $SO_2$-Induced Allylic Oxidation of Cyclohexene with Molecular Oxygen".
Chem. Eng., Sep. 25, 1967, 118–120.
J. Org. Chem., 1980, 45, 40–43, "Liquid-Phase Catalytic Hydrogenation of 1,4-Cyclohexanedione: Activity and Selectivity".
J. Organomet. Chem., 270 (1984) 333–341, "Ruthenium-Catalyzed Oxidation of Alcohols and Catechols Using t-Butyl Hydroperoxide".
Chem. Soc. Jap. Chemistry Letters, pp. 257–260, 1980 "A New Preparative Method for 1,3-Dicarbonyl Compounds by the Regioselective Oxidation of $\alpha,\beta$-Unsaturated Carbonyl Compounds, Catalyzed by $PdCl_2$ Using Hydroperoxides as the Reoxidant of $Pd_0$."
J.C.S. Chem. Comm., 1981, 907–908, "Ruthenium-Catalysed Oxidation of Allyl Alcohols by Molecular Oxygen."
J.C.S. Chem. Comm., 1978, 1099–1100, "$\mu$-Oxobis(-Chlorotripheylbismuth): A Mild Reagent for the Oxidation of the Hydroxy Group, Especially Allylic Alcohols."
J. Org. Chem., vol. 36, No. 6, 1971, "A New Method for the Preparation of $\alpha,\beta$-Unsaturated Carbonyl Compounds."
Ind. J. Chem., 16B, (1978).
J. Org. Chem., 32, 2162 (1967).
Synthetic Comm., 11(4), 295–298 (1981).

Primary Examiner—Werren B. Lone

[57] ABSTRACT

A process for the manufacture of resorcinol is described which relies upon the intermediacy of a $\alpha,\beta$-unsaturated ketone which can be reacted with a hydroxy moiety-containing compound to obtain a resorcinol precursor which is subsequently converted to resorcinol. In a specific embodiment, 2-cyclohexenone is reacted dehydrogenated to resorcinol. In antoher embodiment, 2-cyclohexenone is oxidized to cyclohexane-1,3-dione which is dehydragenated obtain resorcinol.

13 Claims, No Drawings

PROCESS FOR MANUFACTURE OF RESORCINOL

RELATED APPLICATION DATA

This application is a continuation in part of our co-pending and commonly assigned application Ser. No. 840,838, filed on Mar. 18, 1986, now abandoned.

TECHNICAL FIELD

This invention relates generally to the manufacture of resorcinol, and more specifically to a method for establishing meta-orientation of hydroxyl moieties while avoiding the corrosion, energy intensity and co-product liabilities of prior methods.

BACKGROUND OF THE INVENTION

The commercial production of resorcinol must specifically address the isomer problem. Whether starting from benzene, phenol, or non-cyclic compounds, the commercial feasibility of any resorcinol process depends upon its ability to achieve high yields of meta-oriented precursors to enable the conversion to resorcinol.

There are currently two industrial methods for the production of resorcinol, a compound typically used as a synthetic resin component of rescrcinol-formaldehyde resins for rubber and wood glue industries. There are two other routes to resorcinol which potentially could become attractive. One industrially-practiced process is the sulfonation process which is described in *Chem. Eng.*, Sept. 25, 1967. In this process, benzene is sulfonated with oleum to establish meta-orientation (Reaction 1) and then neutralized to obtain a sodium-sulfonic acid salt (Reaction 2) which is further treated with dry caustic to eliminate the sulfonic acid group to form sodium sulfite (Reaction 3) which is then acidified to resorcinol (Reaction 4).

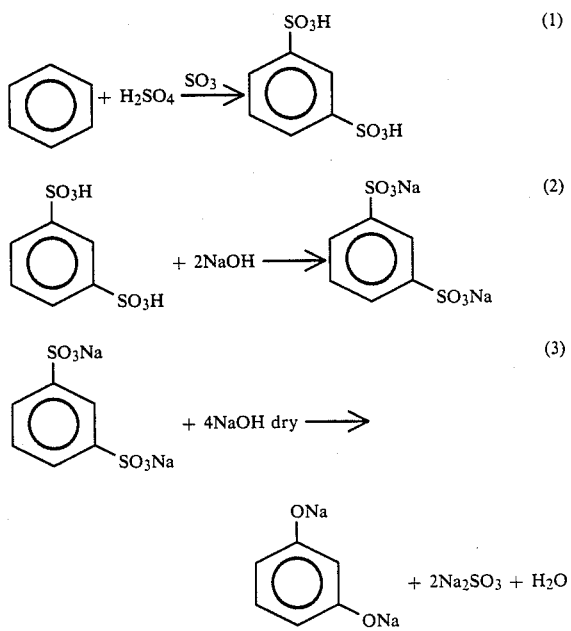

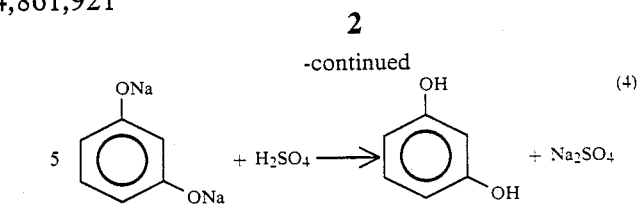

In commercial practice, this process is energy intensive in obtaining dry sodium products (sodium sulfate and sodium sulfite) and is capital intensive due to the corrosion problems connected with sulfuric acid and caustic.

A second industrial process follows the diisopropylbenzene route to resorcinol. See, e.g., U.S. Pat. Nos. 4,347,393, 4,283,570, 4,283,567, 4,273,623, 4,239,921, 4,229,597 and 4,192,958. In this process, propylene is added to benzene to establish meta orientation. (Reaction 5). The para isomer and other propylated species are formed which must be separated and recycled so that high yields of pure meta-product can be obtained. Alternatively, the para isomer can be separately converted to hydroquinone. In the latter case, the process becomes a resorcinol-hydroquinone process. Subsequently, the isopropyl groups are oxidized to obtain hydroperoxide functionality (Reaction 6). This intermediate then converts to resorcinol and acetone (Reaction 7).

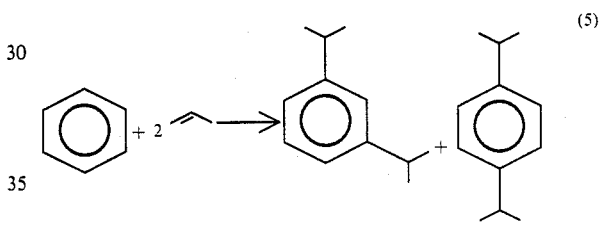

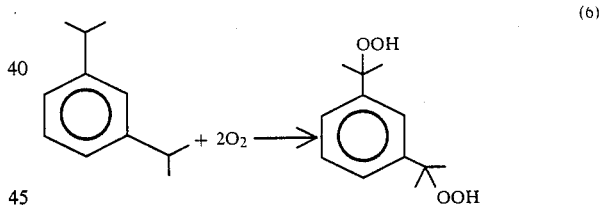

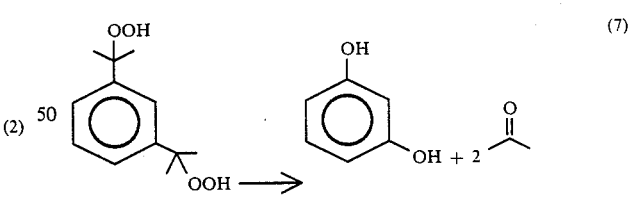

The diisopropylbenzene process suffers from two major drawbacks. First, the addition of propylene to benzene is not a selective reaction so that means for handling unwanted para-isomer products must be employed. Secondly, the economics of this process are largely dependent upon the acetone market which could be a liability if there is an unexpected change in that market.

A third route to resorcinol, which may possibly become commercialized, is described in U.S. Pat. Nos. 3,862,245 and 3,862,246. This process involves the nitration of benzene (Reaction 8) to obtain the desired meta orientation. Dinitrobenzene is then reduced to phenylene diamine (Reaction 9). A substitution reaction then yields resorcinol and ammonium sulfate (Reaction 10).

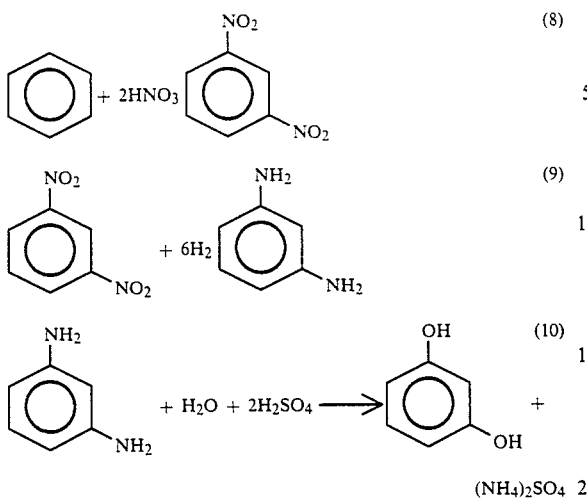

The nitration process is expensive due to the nitration step, produces large quantities of salt, and suffers from yield losses to other isomers.

A fourth process, more recently emerging as a commercial route to resorcinol, and described in U.S. Pat. Nos. 4,397,709 and 4,250,336, involves the condensation of acetone and acrylic acid to form a delta-keto-acid (Reaction 11). This acid is then reacted with an alcohol (Reaction 12) to obtain the keto ester which can be cyclized over palladium/thorium catalyst to obtain resorcinol (Reaction 13).

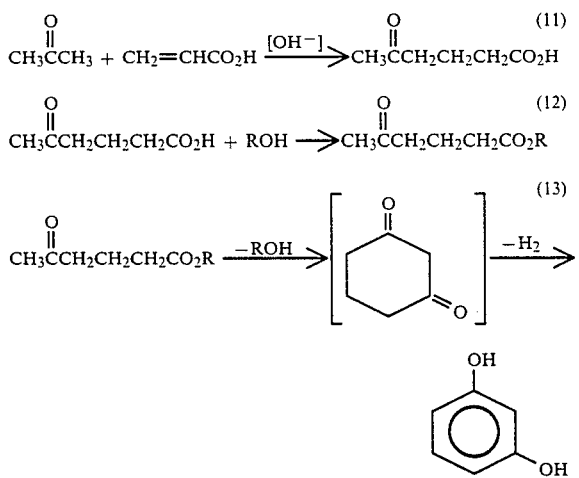

The acetone/acrylic acid process has several drawbacks. Apparently, this process is limited in the Michael addition step due to the formation of by-product mesityl oxide. U.S. Pat. No. 4,397,709 teaches the use of a secondary amine catalyst. U.S. Pat. No. 4,250,336 teaches the combinaton of the cyclization and dehydrogenation steps (Reaction 13). The difficulty in making this process work successfully is catalyst lifetime and recycle of the mesityl oxide.

In summary, prior commercialized resorcinol processes exhibit potential market vulnerability because of co- or by-product formation and capital intensity. The present invention utilizes optimized, selective reactions which yield minimal by-products. The recognition of the intermediary of α,β-unsaturated ketone enables highly selective meta-oriented reactions. Any by-products which may be produced can be conveniently recycled since they are typically substrates for some of the preceding or subsequent reaction steps. In its preferred embodiment, this process advantageously first removes aromatization, fixes the meta-regioselective hydroxyl moiety and subsequently restores aromatization. Therefore, it is an object of this invention to provide a method of manufacturing resorcinol which minimizes co-products or by-products from the reaction steps.

It is a further object of this invention to utilize highly selective reactions for each process step thereby increasing the overall yield for the process.

It is another object of this invention to practice non-corrosive reaction steps thereby reducing the level of capital investment required to construct a plant to practice this invention.

These, and further objects of the invention, will become apparent to those skilled in the art with reference to the description below.

SUMMARY OF THE INVENTION

The present invention is directed to a novel process for the production of resorcinol through the intermediacy of α,β-unsaturated ketones. The lack of aromaticity of the intermediate products permits highly selective, catalytic addition of a hydroxyl moiety in the desired meta position. The α,β-unsaturated ketone may be cyclized, or not, prior to addition of a hydroxyl moiety across the double bond.

In a preferred embodiment, the process involves hydrating 2-cyclohexenone to form 3-hydroxycyclohexanone and dehydrogenating 3-hydroxycyclohexanone to obtain resorcinol. In another embodiment of the process, 2-cyclohexenone is hydrated to form 3-hydroxycyclohexanone which is subsequently dehydrogenated to obtain cyclohexanedione. The dione is then further dehydrogenated to obtain resorcinol. In a third embodiment, 2-cyclohexenone is oxidized to obtain cyclohexane-1,3-dione. The 1,3-dione is then dehydrogenated to obtain resorcinol.

BEST MODE FOR PRACTICING THE INVENTION

While the invention is herein described with reference to the multi-step conversion of phenol to resorcinol, slight modifications and substitutions may be made which are intended to be within the scope of this invention. For example, benzene can be used as the starting material rather than phenol without deviating from the claimed invention. Benzene can be selectively hydrogenated to cyclohexene according to established technology. See, e.g., *J. Molecular Catalysis* 21 (1983) 393–404. Cyclohexene can be directly oxidized to cyclohexanone using catalyst composition described in our pending application serial No. 779,501 assigned to the same assignee as this application. More advantageously, however, cyclohexene can be directly converted to 2-cyclohexenone according to several previously described routes, one of which is described in *J. Org. Chem.*, 1980, 45, 4278–4280. It is also intended that the production of substituted resorcinols through α,β-unsaturated ketone intermediates be within the scope of this invention.

With this background in mind, in the preferred embodiment of the process of this invention, there are four major reaction steps. In the first step, phenol is selectively hydrogenated to cyclohexanone. The second step, through selective oxidative dehydrogenation, converts cyclohexanone to the α,β-unsaturated ketone, 2-cyclohexenone. In the third step, 2-cyclohexenone is hydrated to obtain 3-hydroxy- cyclohexanone which is then oxidatively dehydrogenated to obtain resorcinol in the fourth and final step. Alternative reactions may be substituted for the conversion of 2-cyclohexenone to resorcinol, through cyclohexane-1,3-dione. All of these reactions will be specifically described below.

A. Step One: Phenol to cyclohexanone

Currently, the hydrogenation of phenol to cyclohexanone is practiced commercially. A fairly complete description of this commercial process can be found in R. L. Augustine, editor, *Catalysis of Organic Reactions*, Chapter 20, "Phenol Hydrogenation Process" by Van Peppen, Fisher and Chan (Marcel Dekker, Inc., New York: year of publication); and U.S. Pat. No. 4,200,553 to Van Peppen and Fisher, "Process for Producing Cyclohexanone". While this process practices palladium-catalyzed hydrogenation of phenol in a liquid slurry, vapor phase reactions are also possible.

It is taught by Van Peppen et al. that in order for the liquid slurry conversion process to be commercially viable, the rate of reaction between phenol and hydrogen must be sufficiently fast at practical temperatures. The rate of the reaction is a function of the catalyst used.

Further it is taught that over-hydrogenation of phenol can produce cyclohexanol as a by-product. The hydrogenation catalyst used must therefore be selective. Feedstock phenol, as purchased, is treated to remove catalyst poisons and distilled in a distillation column; subsequently, the distilled phenol and a recycle stream containing the catalyst enter a premixing kettle. Also fed to this kettle are makeup catalyst and, if desired, other chemicals. From the premix kettle, the process stream enters a series of reactors. The hydrogenation is effected by bubbling synthesis gas (75% hydrogen, 25% nitrogen) through the stirred vessels, the catalyst being suspended in the liquid phase by means of mechanical agitation. Hydrogen is consumed as gas and slurry traverse the reactors. As the synthesis gas passes through the liquids, a large part of the product cyclohexanone, being the lowest boiling component in the reaction mixture, is carried along as vapor. The cyclohexanone vapor is condensed and is collected away from the process stream before the gas is passed on to the next reactor stage.

In the last reactor, an overall phenol conversion of about 95% is achieved. The reaction slurry emerging from the last reactor is centrifuged to recover the catalyst for recycle.

Van Peppen et al. teach that the temperature of the hydrogenation step is another critical aspect. Complete avoidance of accidental vapor cloud formation requires that the temperature in each reactor does not exceed the atmospheric boiling point of the mixture in the reactor. To maintain a margin of safety, the temperatures are held no less than five degrees below the prevailing boiling points. The temperature varies between 155° and 170°=C. at pressures of 80 to 220 psig.

The catalyst used in the hydrogenation process consists of palladium on carbon promoted with an alkali metal salt like caustic soda or sodium carbonate. Two distinctly different catalyst species are perceived in this process; (1) a virgin catalyst which is the purchased catalyst added to the first reactor as makeup and (2) the recycle catalyst which is the catalyst in residence in the process loop. The purchased, virgin catalyst contains 5% palladium on carbon support while the palladium content of recycle catalyst is 2.5%. The reaction conditions appear to redistribute the palladium on the surface since the dispersion on recycle catalyst is only about half that of the virgin catalyst.

Virgin catalyst used in this process, contains by specification about 0.8% sodium ion as base. Base is an essential ingredient of the hydrogenation catalyst since it acts as a promoter. The retention of base on the catalyst under the conditions of hydrogenation is relatively poor. In order to maintain adequate catalytic activity, base is added continuously to the process. According to Van Peppen et al., a level of about 0.5 to 1.0% sodium ion as base on the catalyst is desirable.

The continuous addition of base has a substantial impact on the operation of the process and on plant capacity. Without the addition of base, the reaction temperature must be raised by about 30° to 40° C. to maintain conversion at the same throughput.

In general, catalyst deactivating agents enter the process with the reactants. To remove poisons, phenol is treated with a diamine and undergoes multiple distillations. Poisons which have inadvertently entered the process loop may become enriched in the system if recycle streams are not properly controlled. Adsorption of poisons on the catalyst may be either reversible or permanent. At constant levels of poisons in the feedstock, an equilibrium concentration on the catalyst surface is established. Activity of the catalyst and hence, plant capacity, are directly related to this concentration of poisons. In the phenol hydrogenation the major poisons are acids, organic sulfur compounds, iron, and hydroxy-2-propanone.

In summary, cyclohexanone can be manufactured from phenol in high yields throuoh the process described by Van Peppen et al. In the slurry type process, yields of cyclohexanone exceed 98%. High yields and maximum plant capacity are achieved when the activity and the selectivity of the catalyst are maintained at optimum levels. To that end, the catalyst must be continuously promoted by base. Contaminants present in the feedstock which deactivate the catalyst must be eliminated from the feedstock before hydrogenation. Organic acids, iron, sulfur compounds, and acetol are deactivating contaminants of concern in the liquid phase slurry process using cumene-derived phenol. Contamination of the process streams with catalyst poisons is a threat which is recognized, the consequences are understood, and the technology to avoid contamination is in place. This phenol hydrogenation process produces cyclohexanone in a safe and very efficient manner.

EXAMPLE 1

A reduction of phenol was performed at 215° C. and 70 psig, with 0.03 gm. sodium as sodium carbonate per 1000 gm. phenol. After 150 minutes, the reaction yielded 91.5% cyclohexanone and 8% cyclohexanol.

Step 2: Cyclohexanone to 2-cyclohexenone

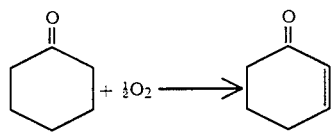

(14)

Dehydrogenation of cyclohexanone is an equilibrium reaction. It has been suggested by M. Okada, Japanese Kokai JP49-127,909 that an analogous reaction can be run without the consumption of hydrogen to drive reaction 14 to the ene,-one product. However, in this preferred embodiment, oxidative dehydrogenation is used to favor the 2-cyclohexenone product. Vapor phase oxidative dehydrogenation over a gold catalyst is described in U.S. Pat. Nos. 3,476,808 and 3,673,255 to Etherington et al. The preferred, liquid phase oxidative dehydrogenation of cyclohexanone is described in R. J. Theissen, "A New Method for the Preparation of α,β-Unsaturated Carbonyl Compounds, " *J. Org. Chem.*, Vol. 36, No. 6, 1971. Theissen describes selectivities of 80-95% to 2-cyclohexenone over palladium(II) catalysts and p-benzoquinone cocatalyst. The palladium compounds which are most active and selective are soluble compounds such as dichlorobis(triphenylphosphine)-palladium(II) and palladium(II)acetylacetonate. Co-catalysts are selected from cupric acetylacetonate, dichlorobis(triphenylphosphine)copper(II) and copper acetate. Organic cocatalysts include p-benzoquinone, but this compound is essentially consumed stoichiometrically.

Liquid phase oxidative dehydrogenation can be carried out in a variety of solvents. A completely homogeneous solution is favored both from the standpoint of reaction rate and catalyst activity. Theissen suggests that neat substrate is the best reaction medium with a Cu(II) cocatalyst. A protonic acid solvent, such as acetic or benzoic acid is best when using p-benzoquinone.

EXAMPLE 2

The use of polyoxoanion chemistry as a dehydrogenation co-catalyst was explored. Pd(TFA)2 was used in conjunction with a series of polyoxoanion co-catalysts. The results of these reactions are set forth in Table 1. As can be seen from these data, there is a pronounced solvent effect with H2O/H2SO4 demonstrating the best performance. The best source of Pd+2 is the TFA salt and the polyoxoanion should be in the acid form.

Step 3: 2-Cyclohexenone to 3-hydroxycyclohexanone

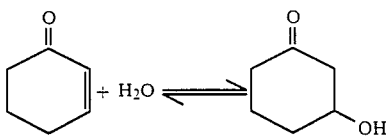

(15)

1,4 addition of water is common to all ene-ones of this type. A process for the hydration of 2-cyclohexenone to 3-hydroxycyclohexanone (Reaction 15) is described in West German Patent No. 2,205,225, assigned to Hoechst. The process described therein calls for passing 2-cyclohexenone and water over an acid or base ion exchanger. Those ion exchange resins which are especially well suited for this hydration are the commercially available, macroporous resins containing sulfuric acid functionality or quaternary hydroxide functionality.

The process first requires that 2-cyclohexenone and water be mixed together. The ratio of components does not seem to greatly affect the reaction. The mixture can be introduced to the ion exchange contact alone, or with a solvent that is inert under reaction conditions such as dioxane, benzene, petroleum ether, tetrachlorodioxide and other ethers. In the preferred embodiment, the mixture of 2-cyclohexenone, water and optional solvent is homogeneous at the reaction temperature. The mixture is prewarmed to the reaction temperature, preferably between 30°-90° C., and then passed over the ion exchange contact which has also been prewarmed to the desired reaction temperature.

The hydration reaction 15 can be viewed as virtually quantitative since the only by-product of the reaction is the substrate itself.

It will also be possible to accomplish the 1,4 addition across the double bond with reactants other than water. For example, under acid catalyzed conditions other hydroxyl-moiety- containing compounds may be used such as alcohols, carboxylic acids, peroxides and peracids.

Alternative routes from the ene,-one, principally oxidation through cyclohexane-1,3-dione, will be described below.

EXAMPLE 3

60 g 2-cyclohexene-1-one and 60 g distilled water were introduced into a jacketed soxhlet extraction ap-

TABLE 1

| RXN[a] | CATALYST/SOLVENT | TEMP | OXYGEN PRESSURE (PSIG) | TIME (HRS) | CONVERSION | SELECTIVITY |
|---|---|---|---|---|---|---|
| 1 | K5H4PMo6V6O40, Pd(TFA)2, H2O/H2SO4 | 85 | 80 | 4 | 37.2 | 14.4 |
| 2 | K5H4PMo6V6O40, Pd(TFA)2, HOAc | 85 | 80 | 4 | 80.0 | 3.7 |
| 3[b] | K5H4PMo6V6O40, Pd(TFA)2, H2O/HOAc | 85 | 80 | 4 | 41.0 | 14.6 |
| 4 | K5H4PMo6V6O40, Pd(TFA)2, H2O/H2SO4 | 85 | 80 | 4 | 36.3 | 17.9 |
| 5[c] | H9PMo6V6O40, Pd(TFA)2, H2O/CH3CN/H2SO4 | 85 | 80 | 2 | 55.7 | 3.4 |
| 6 | H9PMo6V6O40, Pd(TFA)2, H2O/H2SO4 | 85 | 80 | 2 | 44.1 | 13.1 |
| 7 | K5H4PMo6V6O40, Pd(TFA)2, H2O/H2SO4 | 85 | 80 | 2 | 34.2 | 10.7 |
| 8 | K5H4PMo6V6O40, PdSO4.2H2O, H2O/H2SO4 | 85 | 80 | 2 | 48.6 | 3.8 |
| 9 | K5H4PMo6V6O40, Pd(OAc)2, H2O/H2SO4 | 85 | 80 | 2 | 59.3 | 3.1 |
| 10 | H9PMo6V6O40, Pd(TFA)2, H2O/H2SO4 | 85 | 90 | 4 | 35.0 | 20.8 |
| 11 | K5H4PMo6V6O40, Pd(TFA)2, H2O/H2SO4 | 85 | 80 | 4 | 36.3 | 17.9 |
| 12 | Na9PV14O42, Pd(TFA)2, H2O/H2SO4 | 85 | 80 | 4 | 52.9 | 6.2 |

[a] 0.3 mmol heteropolyanion, 0.63 mmol Pd salt, 15 ml H2O, 1.5 ml 1 N H2SO4, 19.3 mmol cyclohexanone
[b] 1.5 ml glacial acetic acid
[c] 7.5 ml H2O, 7.5 CH3CN, 1.5 ml 1 N H2SO4 paratus with a soxhlet thimble containing 50 cc Amberlyst 15 wet cation exchange resin (H+ form) precleaned using multiple hot water extractions. The reaction mixture was at 55° C./ 115 mm Hg for six hours to build up 3-hydroxycyclohexanone. After this time, the solution was distilled to give only unreacted water and 2-cyclohexene-1-one and 37 g of desired product(boiling point=90° C./1 mm Hg). $^{13}C$ NMR of the latter product showed it to be >95% 3-hydroxycyclohexanone (no other material seen by $^{13}C$ NMR or GC). Yield based on 2-cyclohexene-1-one is 57%; selectivity ca. 100%.

Step 4: 3-hydroxycyclohexanone to resorcinol

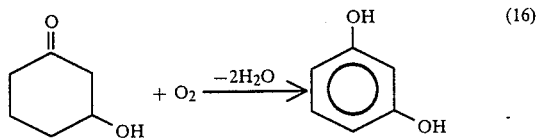

In a prefered embodiment of this process, after the required meta-orientation has been established, aromaticity is restored to the ring by oxidative dehydrogenation (Reaction 16). Kiyoura, in Japanese Kokai JA 51-91215, describes liquid phase, catalytic, oxidative dehydrogenation of 3-hydroxycyclohexanone to resorcinol over a palladium carbon catalyst using air as the molecular oxygen source. Fixed bed or slurry catalyst systems are suggested. Kiyoura further teaches that a reductive environment on the palladium carbon catalyst must be maintained in an oxidative environment.

Canadian Patent No. 951742 to Sugerman discloses an analogous non-oxidative dehydrogenation over copper, chromium, or nickel catalyst in liquid or vapor phase.

EXAMPLE 4

The conversion of 3-hydroxycyclohexanone to resircinol, either oxidatively or non-oxidatively, involves the intermediacy of 1,3-cyclohexanedione. We have shown that 1,3-cyclohexanedione is cleanly dehydrogenated to resorcinol in butyl acetate using the conditions described in U.S. Pat. No. 4,431,848. 0.5 g of a palladium black catalyst with 1.9 g 1,3-cyclohexanedione substrate reacted at 170° C. under nitrogen sparged at ca. 40 ml/min at 90 psig for six hours in butyl acetate. Importantly, the catalyst must first be prereduced dry with hydrogen at room temperature for about one hour before the addition of substrate. With this prereduction, we obtained resorcinol as the major product (>95%) as determined by $^{13}C$ NMR and GC, at about 50% conversion.

A similar reaction using 3-hydroxycyclohexanone showed that in butyl acetate at 160° C. the hydroxyketone decomposed first to give 2-cyclohexene-1-one which effectively disproportionates to cyclohexanone and phenol. Identical results were obtained at lower temperatures. Similar results were obtained using toluene, water and ketones.

In summary, in the preferred embodiment there are four steps:

Step 1: selective hydrogenation

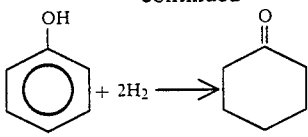

Step 2: selective oxidative dehydrogenation

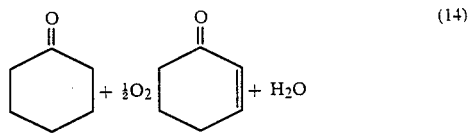

Step 3: 2-cyclohexenone hydration

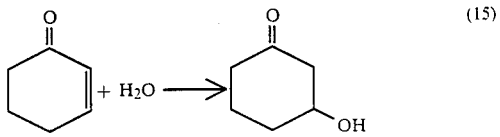

Step 4: Oxidative dehydrogenation of 3-hydroxycyclohexanone

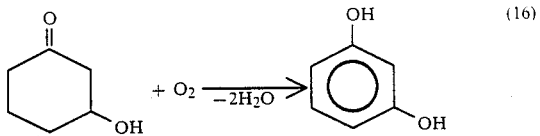

ALTERNATIVE ROUTES TO RESORCINOL

As discussed above, alternative schemes are possible. For example, step 3, hydration, of the α,β-unsaturated ketone can be described in a more general way:

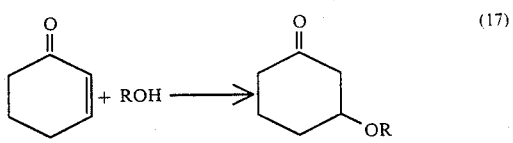

This generalization permits the synthesis of monosubstituted resorcinol products since the dehydrogenation to establish aromaticity (step 4) is not affected by the substitution.

Morrison and Boyd, 2d ed., *Organic Chemistry*, pp. 964–977 detail how ene-ones react with either electrophilic or nucleophilic reagents. The addition of methanol is described as an acid catalyzed, or electrophilic 1,4 addition, across an ene,-one. The acid strength of the electrophile precursor must be sufficient for the reaction to take place. It is well known, and described in the same text, that acidity follows the trend $HCl>HOAc>H_2O>CH_3OH$. Since examples for HCl, $H_2O$ and $CH_3OH$ are described it follows that HOAc should work. Likewise, it follows that the peroxy equivalents would react similarly.

Another alternative scheme which can be predicted to act similarly involves alkyl substituted cyclohexane.

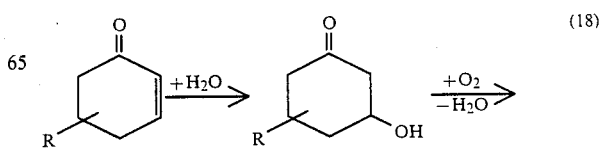

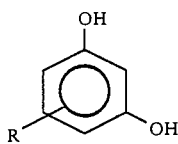

Another embodiment of the process of the instant invention is shown in in Reaction 19:

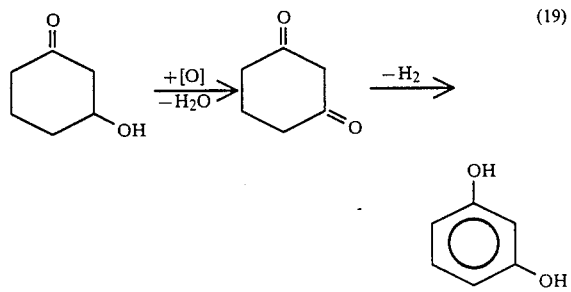

Reaction 19 is an alternative method for converting 3-hydroxycyclohexanone to resorcinol through the 1,3-dione intermediate.

The conversion of 3-hydroxycyclohexanone to cyclohexane-1,3-dione can be carried out by the use of reagents which selectively convert alcohols to ketones, preferably, reagents which specifically convert allylic alcohols to ene-ones. For example, (BiClPh$_3$)$_2$O has been used as a stoichiometric oxidant for the conversion of 3-hydroxycyclohexanone to cyclohexane- 1,3-dione according to a procedure described for similar compounds in *JCS Chem. Comm.* 1099 (1978). Extending the concept of allylic alcohol oxidation further, a RuCl$_2$(PPh$_3$)$_3$ complex can be used in conjunction with an oxidant like tert-butyl hydrogenperoxide (TBHP), or oxygen, to oxidize the hydroxyketone to the dione. These catalysts are described in *J. Organomet. Chem.*, 270 (1984), 333–341 and *JCS Chem. Comm.* (1981) 907-8, respectively.

To test the allylic alcohol hypothesis, we found literature references for two systems which oxidize allylic alcohols to the corresponding ketone. Barton and coworkers (*Chem. Commun.*, 1978, 1099) report that a stoichiometric amount of (BiClPh$_3$)$_2$O oxidizes allylic alcohols cleanly to the 2-ene-ketone.

EXAMPLE 5

We repeated their procedure using 3-hydroxycyclohexanone as the substrate and found that a small amount of cyclohexane-1,3-dione was produced (as evidenced by gas chromatography). In a typical reaction, a 100 mL round bottom flask was charged with 0.285 g 3-hydroxycyclohexanone (2.5 mmol), 1.94 g (BiClPh$_3$)$_2$O (2.0 mmol), 2.00 g K$_2$CO$_3$ and 20 mL dichloromethane. The resultant mixture was stirred at 25° C. in air for 16 hours. GC analysis after this time indicated that 0.236 mmol of cyclohexane-1,3-dione was produced (9.4% yield). Longer reaction times or higher reaction temperatures did not significantly enhance the yield.

A second paper (Tsuji, et al., *J. Organomet. Chem.*, 1984, 270, 333–41) also describes the oxidation of allylic alcohols using TBHP and a noble metal catalyst, preferably RuCl$_2$(PPh$_3$)$_3$.

EXAMPLE 6

In a typical reaction, a 50 mL 3-necked round bottom flask is charged in a glove box with 1.25 g 3-hydroxycyclo-hexanone (10.66 mmol), 0.096 g RuCl$_2$(PPh$_3$)$_3$ (0 1 mmol), 0.0845 g tetradecane as an internal standard and 12 mL acetone. On a schlenk line under argon, TBHP (1.96 g, 15 mmol) is added dropwise over 30 minutes. After addition, the resulting solution is stirred an additional two hours at 25° C. GC analysis after this time showed 1.06 mmol of cyclohexane-1,3-dione produced and 8.60 mmol of unreacted 3-hydroxycyclohexanone. Refluxing the solution an additional two hours gave 1.304 mmol dione and 8.11 mmol hydroxyketone for a conversion of 20% and a selectivity of 65% to the cyclohexane-1,3-dione.

A process for the subsequent dehydrogenation of cyclohexane 1,3 dione to resorcinol is described in United Kingdom Patent No. 1,188,387 to Kirby. The dehydrogenation is accomplished by heating cyclohexane-1,3-dione, in the presence of a catalyst selected from the group consisting of iodine, palladium on charcoal and palladium on calcium carbonate, at a temperature within the range of 150° to 300° C.

Another embodiment of the conversion of cyclohexenone to resorcinol is described in Reaction 20.

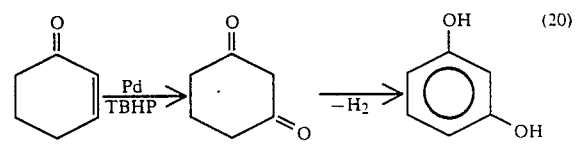

In the first step, the ene-one is converted to the 1,3-dione by regioselective oxidation. Similar regioselective oxidations are described in J. Tsuji et al., "A New Preparative Method for 1,3-Dicarbonyl Compounds by the Regioselective Oxidation of α,β-Unsaturated Carbonyl Compounds, Catalyzed by PdCl2 Using Hydroperoxides as the Reoxidant of Pd°'", *Chem. Soc. Jap.*, Chemistry Letters, pp. 257–260, 1980. Tsuji et al., report the regioselective oxidation of α,β-unsaturated ketones to 1,3 diketones with satisfactory rates and yields. Na$_2$PdCl$_4$ is the preferred palladium salt due to high solubility. t-butyl hydroperoxide and hydrogen peroxide are described as the best palladium reoxidants. Fifty percent acetic acid, isopropyl alcohol and N-methylpyrrolidone are suitable solvents for the liquid phase reaction; temperatures within the range of 50°-80° C. are preferred for this reaction. Following the preparative method of Tsuji, et al., *Chem Lett.* 257 (1980) for β-diketone, we have been able to oxidize 2-cyclohexene-1-one with high yield to cyclohexane-1,3-dione.

EXAMPLE 7

In a typical reaction, the substrate, 2- cyclohexene-1-one (1 mL) was added dropwise to a 12 mL solution of Na$_2$PdCl$_4$.3H$_2$O (0.5 g, 1.5 mmole), t-butyl-hydroperoxide (70%, 2 mL, 14.6 mmole) in 10 mL of aqueous acetic acid (50 volume %) at room temperature. The brown solution was heated to 50° C. and was monitored by GLC. After 8 hours, the reaction was complete and the yields of the dione have been observed to be between 75 and 88%.

EXAMPLE 8

We have shown that cyclohexane-1,3-dione is cleanly dehydrogenated to resorcinol in butyl acetate using the conditions described in U.S. Pat. No. 4,431,848 - 0.5 g of a palladium black catalyst with 1.9 g 1,3-cyclohexanedione substrate reacted at 170° C. under nitrogen sparged at about 40 mL/min at 90 psig for six hours in butyl acetate. Importantly, the catalyst must first be prereduced dry with hydrogen at room temperature for about one hour before the addition of substrate. With prereduction we obtained resorcinol as the major (>95%) product (as determined by GC and $^{13}$C NMR) at about 50% conversion.

SUBSTITUTED RESORCINOL PRODUCTS

As previously noted, hydroxyl containing compounds may be used to add a hydroxyl moiety in the meta-position to cyclohexenone.

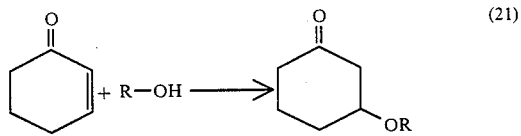

(21)

This product may then be treated further to give monosubstituted resorcinol products. For example, a Schiff Base Reaction can be practiced to obtain an amine,-ol product (Reaction 22).

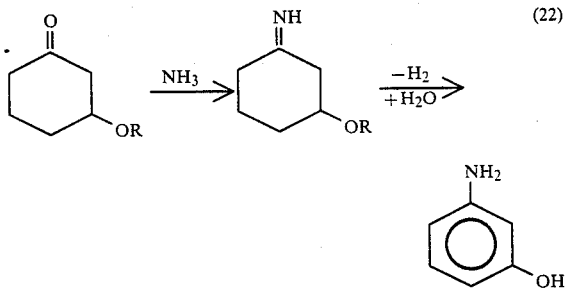

(22)

While this invention has been described with reference to particularly preferred embodiments, these embodiments are intended to provide a description of how this invention may be practiced and not to limit the scope of the claims appended hereto.

We claim:

1. A process for the manufacture of resorcinol which comprises the steps of
   a. reacting an α,β-unsaturated cyclic ketone, under acid-catalyzed conditions, with a hydroxyl-moiety-containing compound selected from the group consisting of water, oxygen, alcohols, carboxylic acids, peroxides and peracids to obtain a cyclic resorcinol precursor having at least six carbon atoms and with meta-oriented hydroxyl moieties; and,
   b. converting said cyclic resorcinol precursor to resorcinol by dehydrogenation, in the presence of a metal catalyst.

2. The process of claim 1 wherein said at least six carbon resorcinol precursor is cyclohexane-1,3-dione.

3. The process of claim 1 wherein said at least six carbon resorcinol precursor is 3-hydroxycyclohexanone.

4. A process for the manufacture of resorcinol which comprises the steps of
   hydrating 2-cyclohexenone to form 3hydroxycyclohexanone under acid catalyzed conditions; and
   oxidatively dehydrogenating 3-hydroxycyclohexanone to obtain resorcinol.

5. A process for the manufacture of resorcinol which comprises the steps of
   hydrating 2-cyclohexenone to form 3-hydroxycyclohexanone under acid catalyzed conditions;
   oxidatively dehydrogenating 3-hydroxycyclohexanone to obtain cyclohexane-1,3-dione; and
   dehydrogenating cyclohexane-1,3-dione to obtain resorcinol.

6. A process for the manufacture of resorcinol which comprises the steps of:
   oxidizing 2-cyclohexenone to form cyclohexane-1,3-dione; and
   dehydrogenating cyclohexane-1,3-dione to obtain resorcinol.

7. The process of claim 1 wherein said α,β-unsaturated cyclic ketone is selected from the group consisting of 2-cyclohexeneone and substituted 2-cyclohexenones.

8. The process of claim 1 wherein said resorcinol precursor dehydrogenation is an oxidative dehydrogenation carried out in the presence of a metal catalyst selected from the group consisting of palladium, platinum, ruthenium and rhodium.

9. The process of claim 1 wherein said resorcinol precursor dehydrogenation is a non-oxidative dehydrogenation carried out in the presence of a metal catalyst selected from the group of metals consisting of copper, chromium, nickel, platinum, palladium, ruthenium and rhodium.

10. The process of claim 1 wherein said reaction between an α,β-unsaturated ketone and a hydroxyl-moiety containing compound is performed in the presence of a macroporous ion exchange resin containing sulfuric acid functionality 11. The process of claim 1 wherein said reaction between an α,β-unsaturated ketone and a hydroxyl-moiety containing compound is performed in the presence of a macroporous ion exchange resin containing quaternary hydroxide functionality.

12. A process for the manufacture of resorcinol which comprises the sets of
   (i) hydrogenating phenol to form cyclohexanone using a noble metal catalyst;
   (ii) oxidatively dehydrogenating cyclohexanone to form 2-cyclohexenone using a noble metal catalyst;
   (iii) hydrating 2-cyclohexenone to form 3-hydroxycyclohexanone under acid catalyzed conditions; and
   (iv) oxidatively dehydrogenating 3-hydroxycyclohexanone to obtain resorcinol.

13. A process for the manufacture of resorcinol which comprises the steps of
   (i) oxidatively dehydrogenating cyclohexanone to form 2-cyclohexenone using a noble metal catalyst;
   (ii) hydrating 2-cyclohexenone to form 3-hydroxycyclohexanone under acid catalyzed conditions; and
   (iii) oxidatively dehydrogenating 3-hydroxycyclohexanone to obtain resorcinol.

* * * * *